(12) United States Patent
Randel

(10) Patent No.: US 11,464,818 B2
(45) Date of Patent: *Oct. 11, 2022

(54) CANNABINOIDS INFUSED CONSUMABLES

(71) Applicant: Michael William Randel, Lakebay, WA (US)

(72) Inventor: Michael William Randel, Lakebay, WA (US)

( * ) Notice: Subject to any disclaimer, the term of this patent is extended or adjusted under 35 U.S.C. 154(b) by 209 days.

This patent is subject to a terminal disclaimer.

(21) Appl. No.: 17/039,787

(22) Filed: Sep. 30, 2020

(65) Prior Publication Data

US 2022/0096581 A1    Mar. 31, 2022

(51) Int. Cl.
| | | |
|---|---|---|
| *A61K 36/00* | (2006.01) |
| *A61K 36/185* | (2006.01) |
| *A61K 47/44* | (2017.01) |
| *A61K 47/46* | (2006.01) |

(52) U.S. Cl.
CPC ............ *A61K 36/185* (2013.01); *A61K 47/44* (2013.01); *A61K 47/46* (2013.01); *A61K 2236/31* (2013.01); *A61K 2236/37* (2013.01)

(58) Field of Classification Search
None
See application file for complete search history.

(56) References Cited

U.S. PATENT DOCUMENTS

| | | |
|---|---|---|
| 10,028,987 B1 | 7/2018 | Pillsbury |
| 10,103,225 B2 | 10/2018 | Reillo et al. |
| 2017/0196923 A1 | 7/2017 | Moore |
| 2018/0200315 A1 | 7/2018 | Silver |

FOREIGN PATENT DOCUMENTS

| | | |
|---|---|---|
| CA | 2859930 A1 | 3/2016 |

*Primary Examiner* — Michael V Meller
(74) *Attorney, Agent, or Firm* — Thomas LaGrandeur

(57) ABSTRACT

The present disclosure is directed to cannabinoids infused coffee beans, nuts, and seeds consumables and methods of producing the cannabinoid infused consumables. The consumables are infused in an overall two-step process, in which cannabinoids from a *Cannabis* species are first infused into coconut oil, which in turn is used to infuse a consumable of choice with cannabinoids to generate the cannabinoids infused consumables.

12 Claims, 3 Drawing Sheets

CANNABINOIDS INFUSED CONSUMABLES

FIELD OF THE INVENTION

The invention relates to whole *Cannabis* infused coconut oil which in turn is used to infuse coffee beans, nuts, and seeds.

BACKGROUND

*Cannabis* has been used to alleviate stress and other illnesses caused by posttraumatic stress disorder, seizures, epilepsy, multiple sclerosis, and the like. *Cannabis*, commonly known as marijuana or hemp, is a genus of flowering plants that includes at least three species, *Cannabis sativa*, *Cannabis indica*, and *Cannabis ruderalis*.

*Cannabis* plants produce a variety of potentially useful or beneficial cannabinoids, which produce mental and physical effects when consumed. Cannabinoids are a chemical group or family of 21-carbon-containing terpenophenolic compounds produced by *Cannabis* species. Current estimates of the number of cannabinoids found in *Cannabis* species is well in excess of 100 different cannabinoids. Two of the most prominent cannabinoids are Cannabidiol (CBD) and Tetrahydrocannabinol (THC). In addition to CBD and THC, other cannabinoids such as cannabichromene (CBC), cannabigerol (CBG), cannabinol (CBN), and others are present in varying amounts in *Cannabis* plant material.

Commonly consumed sources of cannabinoids include extracts, oils, isolates, and the like from *Cannabis* species including marijuana, hemp, and industrial hemp, which contains a THC content of less than 0.3% of overall mass. While providing useful or beneficial effects to the user, such extracts, oils, and isolates are typically found to have undesirable tastes, flavors, odors, and/or other unfavorable attributes. In particular, cannabinoids from extracts or isolates have been added to coffee for consumption in a beverage. The addition of cannabinoid containing extracts or isolates to coffee typically imparts an undesirable taste to coffee, since the extracts or isolates typically have an undesirable taste.

Accordingly, there exists a need in the art for consumable cannabinoid-containing coffee beans and resultant beverages that do not have the tastes and odors of typically consumed sources of cannabinoid. In addition, there is a need for cannabinoid-containing nuts and seeds. The presently disclosed cannabinoid-containing coffee beans, nuts and seeds along with methods of preparing such consumables address this need.

SUMMARY

The present disclosure provides for orally ingestible, cannabinoid infused coffee beans, nuts and seeds and methods of producing such. The coffee beans in turn may be used for producing coffee beverage consumables.

The method disclosed entails an overall two-step process in which coconut oil is first infused with cannabinoids from a species of *Cannabis*. In the second step, the cannabinoid infused coconut oil is used to infuse a given food to generate a cannabinoid infused food consumable. The cannabinoid infused coffee beans can be used to generate a cannabinoid infused coffee beverage.

An overall preferred embodiment of generating cannabinoid infused coffee beans, nuts and seeds is presented herein. As detailed below, the method involves a series of steps of heating and cooling/freezing coffee beans, nuts and seeds in the presence of a source of cannabinoids (either *Cannabis* buds or coconut oil) to produce a cannabinoid infused consumable.

The presently disclosed cannabinoid infused coffee beans, nuts and seeds are more fully described in the detailed description below.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF EXEMPLARY EMBODIMENTS

As is known in the art, cannabinoid is a class of chemical compounds found in plants in the *Cannabis* family (e.g., hemp, marijuana, etc.). To date, at least 113 cannabinoids have been identified, accounting for up to 40% of the plant's extract. Well known cannabinoids include Cannabidiol (CBD), Tetrahydrocannabinol (THC) among others, each of which may include a variety of health benefits.

In general, the presently disclosed consumables relate to coffee beans, nuts and seeds, along with and resultant coffee beverages that provide a source cannabinoids, as well as methods of making such coffee beans. The presently disclosed coffee beans are infused with cannabinoids in a way that increases the levels and quantities of cannabinoids transferred to the coffee beans while reducing undesirable tastes, flavors, odors and the like typically associated with and found in commonly used cannabinoid extracts, oils, isolates, edibles and such.

As used herein, the term "infused cannabinoids" or "cannabinoid infused" refers to various foods and/or drinks to which cannabinoids have been infused by a method(s) disclosed herein. The infusion method generally involves preparing a mixture made with whole *Cannabis* plant materials and coconut oil (or similar oil) under specific heating and cooling conditions, and then in turn using the infused oil mixture to infuse coffee beans, roasted nuts, and roasted seed as detailed herein. Throughout this specification, cannabinoid infused food and/or drink may be referred to as "cannabinoid infused" or simply "infused," such as "cannabinoid infused coffee beans" or "infused coffee beans."

Figure 1:
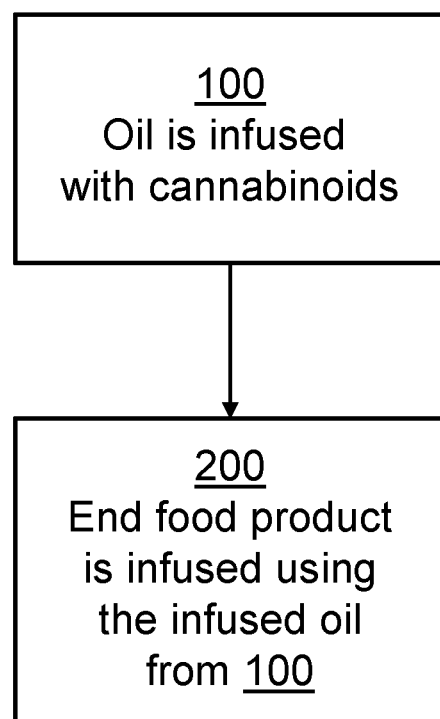
FIG. 1 shows example steps of a method according to exemplary embodiments hereof.

In some embodiments as shown in FIG. 1, cannabinoid infused foods and/or drinks prepared by the methodology disclosed herein are generated in an overall two-step process. In the first step (at 100), whole *Cannabis* plant material is ground and used to infuse an oil, preferably coconut oil, with cannabinoids. Note that because whole *Cannabis* plant material is used at 100, the resulting mixture may be referred to as a full spectrum *Cannabis* and oil mixture. In a second step (at 200), the infused coconut oil is used to infuse an end food product, such as coffee beans, roasted nuts, or roasted seeds with cannabinoids. After the end product is infused with cannabinoids, it may be consumed in any typical fashion, such as direct consumption, used to make a beverage as in the case of coffee beans, and so forth.

Consumption of the cannabinoid food and drink consumables generated by the methods described herein provides the beneficial effects generally associated with cannabinoids. These effects include, but are not limited to, mental and physical effects, such as pain relief from CBDs and other cannabinoids, mental high from THC (in foods infused with marijuana cannabinoids), and other effects attributed to consumption of cannabinoids.

Figure 2:
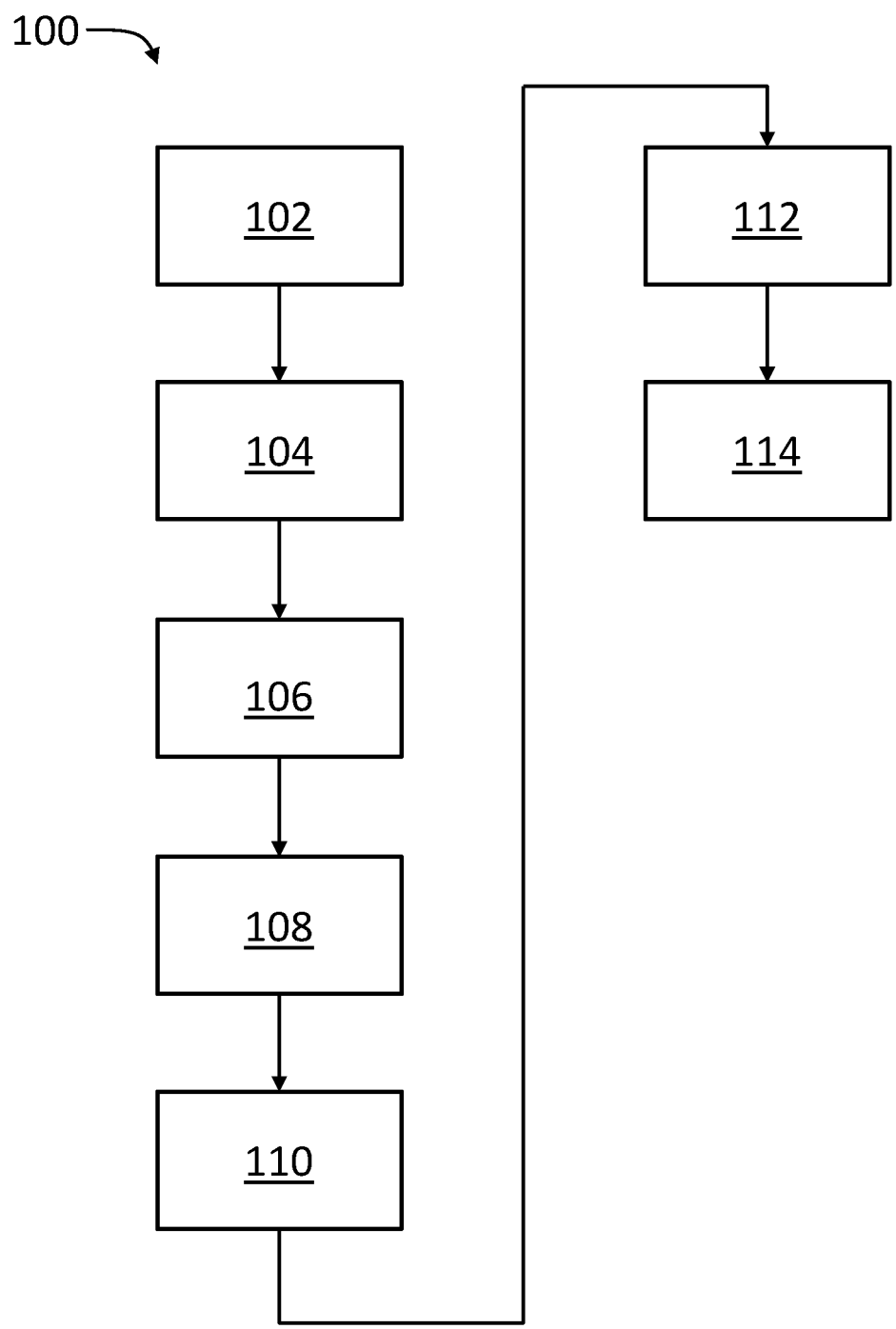
FIG. 2 shows example steps of a method according to exemplary embodiments hereof.

FIG. 2 refers to steps that may be taken to infuse an oil (e.g., coconut oil or a combination of coconut oil and MCT oil (medium chain triglycerides oil)) with cannabinoids to complete step 100 of FIG. 1. Additional oils that can be used in the process include MCT oil, vegetable oil, sunflower oil, olive oil, grape seed and combinations thereof. In one embodiment as shown in FIG. 2, whole, raw *Cannabis* plant material (e.g., flowers, buds, leaves or other plant material; preferably buds) is frozen, preferably for 24 hours (at 102). The *Cannabis* plant may include *Cannabis sativa, Cannabis indica, Cannabis Ruderalis*, other types of *Cannabis* and any combination thereof. The *Cannabis* may be classified as marijuana, hemp, and/or other types of *Cannabis*.

Next (at 104), coconut oil, MCT oil, a combination of coconut oil and MCT oil (or similar oil) is heated to a temperature equal to or between 150° and 200° F., and preferably to about 175° F. For the purposes of this specification, the term "about" used in relation to temperatures will mean within ±1%. Regarding a combination of coconut oil and MCT oil, a preferred embodiment is to use a ratio of 75% coconut oil to 25% MCT oil.

Next (at 106), the *Cannabis* (preferably buds) is added to the coconut oil and held at the temperature (e.g., preferably at about 175° F.) for 4-8 hours (preferably 8 hours), while occasionally (and/or continuously) stirring the mixture. In some embodiments, the ratio of plant material to coconut oil is 1 lb plant material to 2 gallons oil. For example, on a commercial scale, 100 lbs plant material/buds may be mixed with 200 gallons of oil. However, other ratios within 10%, 20%, 30%, 40%, 50%, 75%, 100% of this ratio also may be used. In general, the ratio will be chosen to provide the desired concentration(s) of cannabinoids within the oil.

After this (at 108), the *Cannabis* and coconut oil mixture is frozen for 8-12 hours, and preferably for about 12 hours.

Then (at 110), the *Cannabis* and coconut oil mixture reheated to 150° to 200° F., and preferably to about 175° F., and held at the temperature for a sufficient period of time to liquify the mixture, typically for about 2-4 hours.

Next (at 112), the *Cannabis* and coconut mixture is strained using a press bag (or other suitable straining techniques) and the strained material is separated.

In a further step (114), the strained, cannabinoid infused oil is heated to 250° F. for 2 hours. This step will decarboxylate the carboxylated cannabinoids in the oil, such as CBD-A or THC-A.

This method results in a in a cannabinoid infused oil mixture that may be used for direct consumption and/or for use in infusing other end products with cannabinoids as described below.

Figure 3:
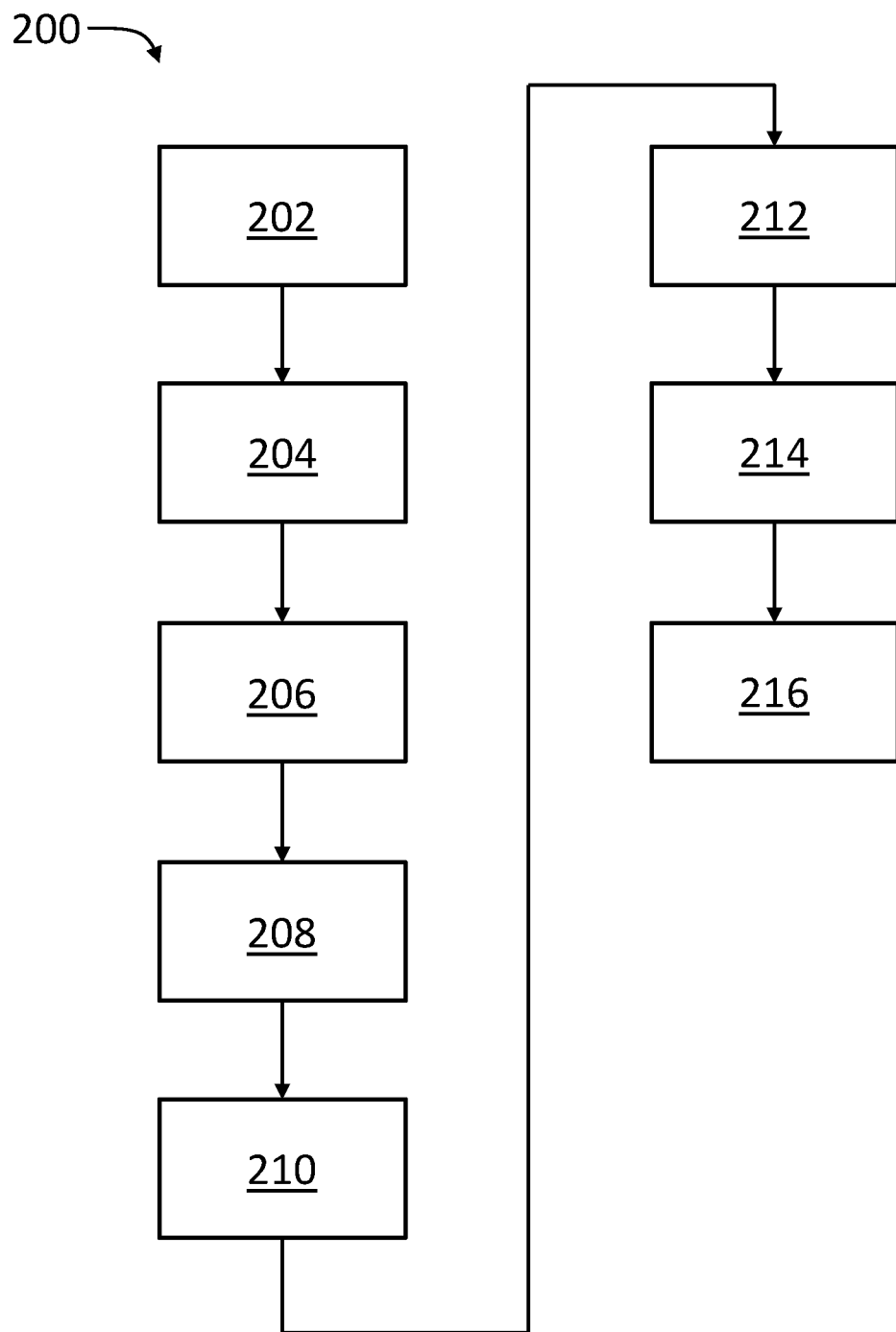
FIG. 3 shows example steps of a method according to exemplary embodiments hereof.

In another embodiment as shown in FIG. 3, a *Cannabis* and coconut mixture, such as the mixture obtained from the process 102-114 (FIG. 2) described above, is used to infuse consumable products such as coffee beans, roasted nuts, and roasted seeds.

First (at 202), at least a portion of the strained *Cannabis* and coconut oil mixture obtained from 102-114 (FIG. 2) is heated to a first temperature equal to or between 175° F. and 185° F.

Next (at 204), a selection of coffee beans, nuts, or seeds (the nuts and seeds may be raw or roasted) is added and stirred into the mixture and held at the first temperature (e.g., preferably about 175° F. to 185° F.) for about 8-9 hours. In the case of coffee beans, the beans preferably are used two or more days after roasting of the beans to allow for chemical release (degassing) of the coffee beans. For the purposes of this specification, the term "about" used in relation to periods of time will mean±3%. Referring to a commercial scale as described above in, which 200 gallons of starting oil was mixed with 100 lbs of plant material, this step will occur in a 400 gallon stock pot.

Next (at 206), the mixture including the coffee beans, nuts, or seeds is frozen for about 8-10 hours. On a commercial scale, this step can be carried out by covering the 400 gallon stock pot with a freezer blanket that will rapidly freeze the mixture and keep it frozen. Alternatively, the material can be rapidly frozen in a blast freezer.

Then (at 208), the mixture including the coffee beans, nuts, seeds, etc., is heated to a second temperature equal to or between 175° F. and 185° F., and held at the second temperature for about 8-9 hours.

Next (210), the mixture including the coffee beans, nuts, or seeds is frozen for about 8-10 hours, as described above for step 206.

Then (at 212), the mixture including the coffee beans, nuts, or seeds is heated to a third temperature equal to or between 100° F. and 150° F., and held at the third temperature for a sufficient period of time to liquify the oil, typically about 2-4 hours, and preferably for about 2 hours.

After this (at 214), the mixture is strained (using any suitable straining techniques) and the coffee beans, nuts, or seeds are removed.

Then (at 216), the coffee beans, nuts, or seeds are then frozen, such as in a blast freezer, and stored frozen for subsequent use/consumption.

This process 202-216 (FIG. 3) results in a selection of coffee beans, nuts, or seeds infused with cannabinoids thereby producing cannabinoid infused coffee beans, nuts, or seeds.

In some embodiments, the freezing steps at 206 and/or at 210 provide organic pressure to the coffee beans, roasted nuts, or roasted seeds that deepens the physical depth of the cannabinoid infusion into the consumables. For example, in some embodiments, the freezing steps at 206 and/or at 210 cause the cannabinoids to be pressed 10%, 20%, 30%, 40%, 50%, 60%, 70%, 80%, 90% and/or 100% to the center of each consumable (that is, to the center of each coffee bean, each nut, each seed, etc.).

It is understood that the acts described above are meant as a general overview and demonstration of an exemplary method, and that the method may include different and/or additional acts as described herein or otherwise.

While the present invention has been described as having particular configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

It is understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first," "second," and so on, in the description and claims, are used to distinguish or identify, and not to show a serial or numerical limitation. Similarly, letter labels (e.g., "(A)", "(B)", "(C)", and so on, or "(a)", "(b)", and so on) and/or numbers (e.g., "(i)", "(ii)", and so on) are used to assist in readability and to help distinguish and/or identify, and are not intended to be otherwise limiting or to impose or imply any serial or numerical limitations or orderings. Similarly, words such as "particular," "specific," "certain," and "given," in the description and claims, if used, are to distinguish or identify, and are not intended to be otherwise limiting.

As used herein, including in the claims, the terms "multiple" and "plurality" mean "two or more," and include the case of "two." Thus, e.g., the phrase "multiple ABCs," means "two or more ABCs," and includes "two ABCs." Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" or "approximately 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

The invention claimed is:

1. A method of infusing an orally ingestible consumable with at least one cannabinoid, the method comprising:
   (A) providing *Cannabis;*
   (B) freezing the *Cannabis* for about 24 hours;
   (C) providing an orally ingestible oil at a temperature of 150° F.-200° F.;
   (D) adding at least a portion of the *Cannabis* of (B) to the oil of (C) to form a first *Cannabis* and oil mixture;
   (E) keeping the *Cannabis* and oil mixture of (D) at a temperature of 150° F.-200° F. for 4-8 hours;
   (F) freezing the *Cannabis* and oil mixture of (E) and keeping it frozen for 8-12 hours;
   (G) heating the *Cannabis* and oil mixture of (F) to a temperature of 150° F.-200° F. for 2-4 hours;
   (H) straining the *Cannabis* and oil mixture of (G) to separate the oil from the *Cannabis* to yield a cannabinoids infused orally ingestible oil;
   (I) heating the cannabinoids infused oil of (H) to a temperature of 250° F. for 2 hours;
   (J) adding an orally ingestible consumable to the cannabinoids infused oil of (I) to form a consumable and infused oil mixture;

(K) heating the mixture of (J) to a temperature of 175° F.-185° F. for 8-9 hours;
(L) freezing the mixture of (K) for 8-10 hours;
(M) heating the mixture of (L) to a temperature of 175° F.-185° F. for 8-9 hours;
(N) freezing the mixture of (M) for 8-10 hours;
(O) heating the mixture of (N) to a temperature of 100° F.-150° F. for 2-4 hours; and
(P) straining the consumable from the infused oil of (O) to yield an orally ingestible consumable infused with at least one cannabinoid, wherein the orally ingestible consumable is selected from the group consisting of coffee beans, raw nuts, and roasted nuts, and the orally ingestible oil is a food grade oil.

2. The method of claim 1, wherein the *Cannabis* provided in (A) is selected from the group consisting of *Cannabis Sativa*, *Cannabis* Indica, and *Cannabis Ruderalis*.

3. The method of claim 1, wherein the oil provided in (C) is selected from the group consisting of coconut oil, medium chain triglycerides oil, and a combination thereof.

4. The method of claim 1, wherein the oil provided in (C) is a mixture of coconut oil and medium chain triglycerides oil at a ratio of 75% coconut oil to 25% medium chain triglycerides oil.

5. The method of claim 1, wherein the oil provided in (C) is coconut oil.

6. The method of claim 1, wherein the orally ingestible consumable is coffee beans.

7. The method of claim 1, wherein the orally ingestible consumable is coffee beans that have been degassed for at least two days following roasting of the coffee beans.

8. The method of claim 1, wherein the orally ingestible consumable is raw nuts.

9. The method of claim 1, wherein the orally ingestible consumable is roasted nuts.

10. The method of claim 1, wherein the *Cannabis* and oil are provided at a ratio of 1 pound of *Cannabis* to 2 gallons of oil in (D).

11. The method of claim 1, wherein the *Cannabis* and oil are provided at a ratio ranging from 10%, 20%, 30%, 40%, 50%, 75%, to 100% of 1 pound of *Cannabis* to 2 gallons of oil in (D).

12. The method of claim 1, wherein the *Cannabis* in (A) is buds of *Cannabis*.

\* \* \* \* \*